United States Patent [19]

Brouwer

[11] Patent Number: 5,384,097
[45] Date of Patent: Jan. 24, 1995

[54] SPECIMEN CONTAINER

[76] Inventor: Emilio A. Brouwer, 6061 Collins Ave. #17-F, Miami Beach, Fla. 33140

[21] Appl. No.: 96,349

[22] Filed: Jul. 23, 1993

[51] Int. Cl.$^6$ .............. B01L 3/00; B65D 69/00
[52] U.S. Cl. ....................... 422/102; 422/61; 422/104; 73/864.91; 206/446; 206/569; 206/805
[58] Field of Search .............. 422/61, 102, 104; 436/66; 73/864.91; 206/363, 364, 438, 446, 569, 570, 805

[56] References Cited

U.S. PATENT DOCUMENTS

| | | | |
|---|---|---|---|
| 2,835,246 | 5/1958 | Boettger | 73/864.91 X |
| 3,768,979 | 10/1973 | Mead et al. | 422/61 |
| 4,046,015 | 9/1977 | Riedl et al. | 73/864.91 |
| 4,707,450 | 11/1987 | Nason | 422/61 X |
| 4,770,853 | 9/1988 | Bernstein | 422/102 |
| 4,849,173 | 7/1989 | Chang | 436/66 X |
| 4,859,610 | 8/1989 | Maggio | 436/66 X |
| 4,978,504 | 12/1990 | Nason | 422/61 |
| 4,989,678 | 2/1991 | Thompson | 175/20 |
| 5,149,506 | 9/1992 | Skiba et al. | 422/102 |
| 5,198,365 | 3/1993 | Grow et al. | 436/66 |

Primary Examiner—Donald E. Czaja
Assistant Examiner—Milton I. Cano
Attorney, Agent, or Firm—J. Sanchelima

[57] ABSTRACT

A kit for collecting specimens that includes a trocar member 20 which is partially housed, at its ends, by jacket members 30 and 40 and rubber band 50 wrapped around jacket members 30 and 40. The first alternate embodiment includes trocar 30' which has a porous lateral wall or the lateral wall includes small apertures so that the moisture can escape thereby permitting a user to do an occult blood test. The second alternate embodiment corresponds to trocar 30" that includes larger apertures around its lateral wall. The second alternate embodiment is intended to be used in hystopathological procedures. A mixer member is coaxially mounted within either jacket member 30 or 40. A reagent is preferably stored in the other jacket not having the mixer member.

2 Claims, 3 Drawing Sheets

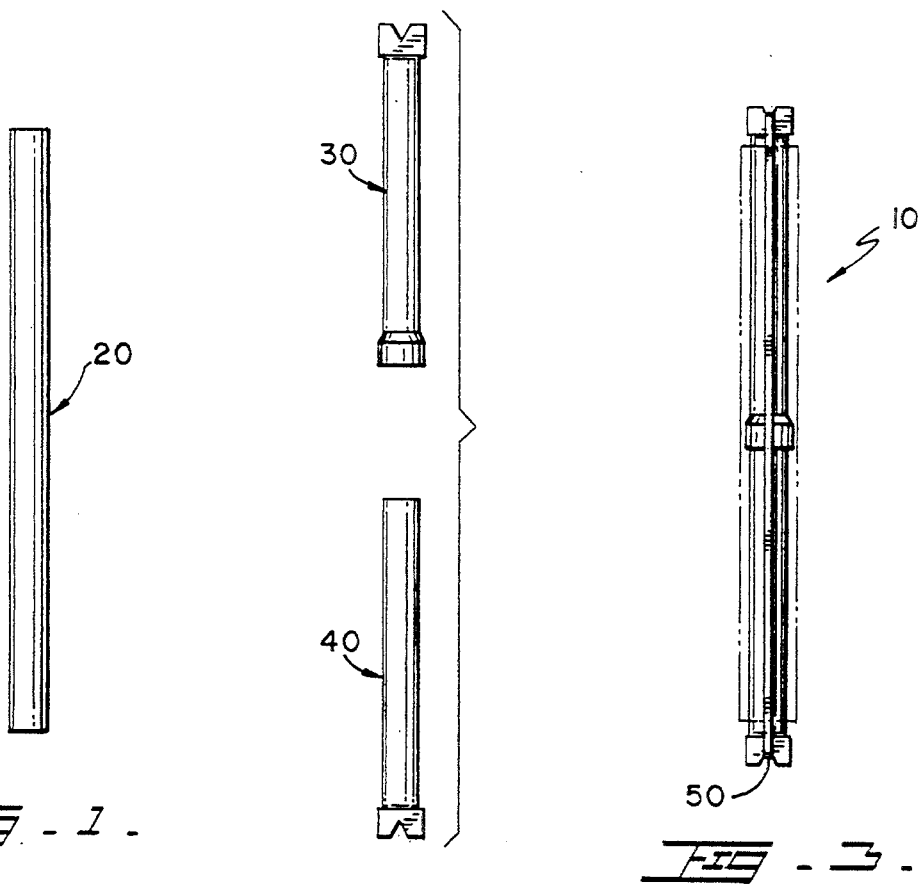
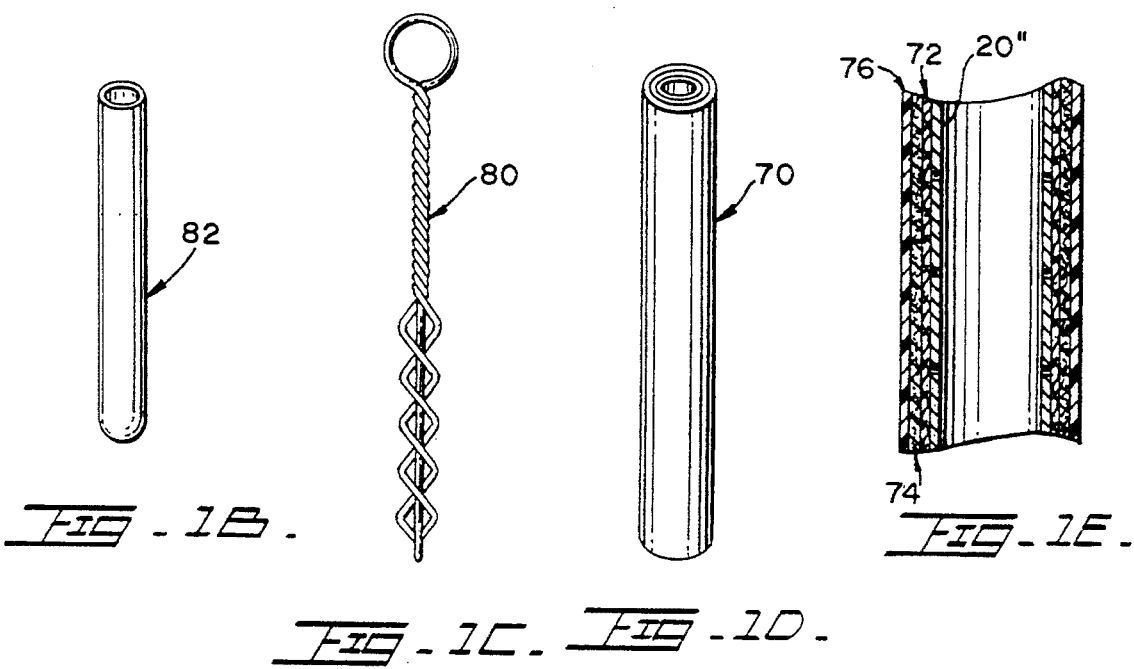

SPECIMEN CONTAINER

BACKGROUND OF THE INVENTION

1. Field of the Invention.

The present invention relates to fecal specimen containers, and more particularly, to those containers that are disposable.

2. Description of the Related Art.

Applicant believes that the closest reference corresponds to U.S. Pat. No. 4,707,450 issued to Frederic Nason in 1987. However, it differs from the present invention because it uses a swab tip that can only take a specimen from the outer surface of the material being examined. It fails to disclose the jackets, mixer and any of the other elements claimed and described below.

Other patents describing the closest subject matter provide for a number of more or less complicated features that fail to solve the problem in an efficient and economical way. None of these patents suggest the novel features of the present invention.

SUMMARY OF THE INVENTION

It is one of the main objects of the present invention to provide a kit for readily collecting specimens from a mass of material and the kit being suitable for mailing with the attendant manipulation.

It is another object of this invention to provide such kit that can readily be used to obtain a sample across the entire mass of the material being tested.

It is still another object of the present invention to provide a kit that can contain the reactive agents for the specimens' processing.

It is yet another object of this invention to provide such a device that is inexpensive to manufacture and maintain while retaining its effectiveness.

It is still another object of this invention to provide a kit that permits a user to test the specimen for occult blood.

Further objects of the invention will be brought out in the following part of the specification, wherein detailed description is for the purpose of fully disclosing the invention without placing limitations thereon.

BRIEF DESCRIPTION OF THE DRAWINGS

With the above and other related objects in view, the invention consists in the details of construction and combination of parts as will be more fully understood from the following description, when read in conjunction with the accompanying drawings in which:

FIG. 1 represents the preferred embodiment for a trocar used with the kit subject of the present application. This trocar can be made of a porous or non-porous material.

FIG. 1B shows a non-porous jacket to be used to cover porous trocars so that the specimen can be stiffed and mixed with reagents without coming in contact with a user's fingers.

FIG. 1B represents a stirrer member to be used to mix the specimen with reagents inside a porous trocar.

FIG. 1D shows the soft jacket used with porous trocars to filter the liquid resulting from the mixture of the specimen and absorbing the filtered liquid by an absorbent paper.

FIG. 1E represents a partial enlarged cross-sectional view of the soft jacket shown in FIG. 1D showing the different filtering layers.

FIG. 2 is a representation of the two jacket members used in the preferred embodiment of the kit.

FIG. 3 shows the kit, after a specimen has been collected, with a rubber band urging both jacket members against each other with a paper from the identification of the specimen wrapped around the jacket members.

DETAILED DESCRIPTION OF THE PREFERRED EMBODIMENT

Referring now to FIGS. 1; 2 and 3, where a preferred embodiment for the present invention is generally referred to with numeral 10, it can be observed that it basically includes trocar member 20 which is partially housed at its ends, when assembled by jacket members 30 and 40 and rubber band 50 longitudinally wrapped around jacket members 30 and 40. The preferred embodiment is intended to be used primarily with fecal specimens to be tested for parasites.

Figure 4:
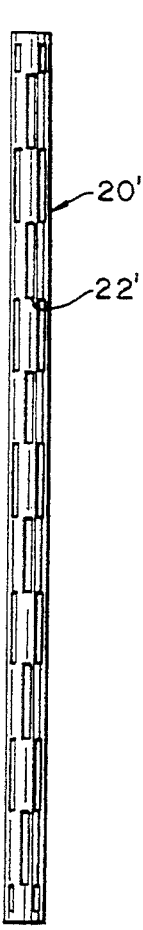
FIG. 4 shows a first alternate embodiment for a trocar element used in the present invention having a lateral surface with perforations.
Figure 6:
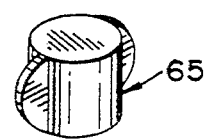
FIG. 6 is an isometric representation of the cap member used in the trocar shown in FIG. 5.
Figure 5:
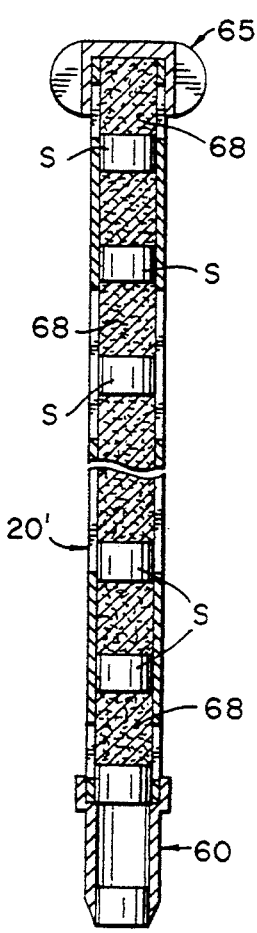
FIG. 5 illustrates a cross-section of the trocar shown in FIG. 4 with a blade member on one end and a cap member on the other end.

The first alternate embodiment, as shown in FIGS. 4 and 5, includes trocar member 20' which has a lateral wall with perforations 22' so that the chemicals can come in contract with the specimens thereby permitting a user to fix the tissues for hystopathological procedures. This first alternate embodiment is used for tissues. Cutting blade member 60 is removably mounted to one end of trocar 20'. Cutting blade member 60 is basically a tubular body with a sharp peripheral cutting edge. Cap member 65 is removably mounted to the other end of trocar 20'. Tissue specimens are cut when blade member 60 is pressed against it perpendicularly. Initially, dividing member 68 is inserted then a tissue specimen S is cut and pushed up through trocar member 20'.

Figure 9:
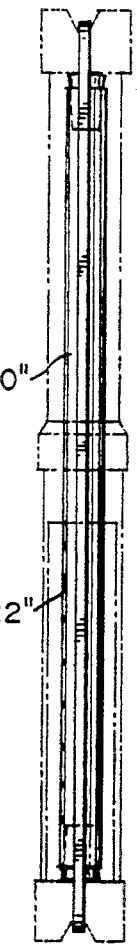
FIG. 9 is an elevational view of an alternate embodiment used for occult blood specimens wherein the trocar used is either porous or contains perforations.
Figure 7:
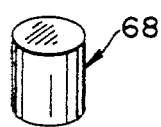
FIG. 7 shows a specimen divider.
Figure 8:
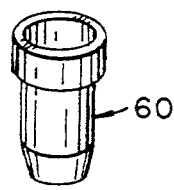
FIG. 8 shows an isometric representation of the blade member used in the trocar shown in FIG. 5.
Figure 10:
FIG. 10 shows an isometric representative of the cap member used with the trocar shown in FIG. 9.
Figure 11:
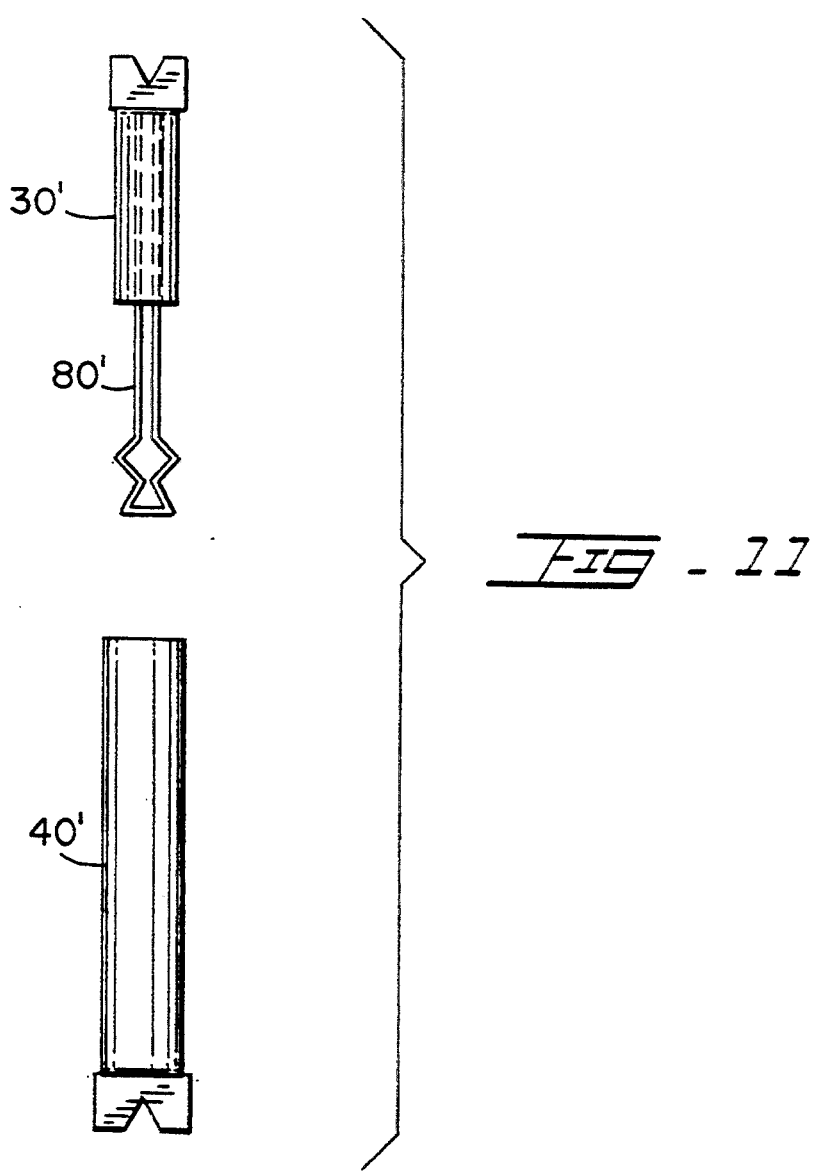
FIG. 11 is a representation of two jacket members with one of the jackets including a coaxially disposed stirrer member.

The second alternate embodiment, as shown in FIG. 9, corresponds to trocar 20" that includes small apertures 22" around its lateral wall or it could even be a porous lateral wall. If trocar 20" is made out of a porous material, it looks very similar to trocar 20. The objective being that for occult blood testing, stirrer member 80 needs to be used to mix the reagents with the specimen and the liquid part and/or moisture is permitted to flow out through the lateral wall of trocar 20". A user introduces stirrer member 80 and mixes the specimen with reagents that are already contained inside trocar 20", in the preferred embodiment. However, it is also possible to add the reagents after the specimens are collected. It is, however, more practical if the reagents are already contained in the trocar. A user inserts trocar 20" in non-porous jacket 82. Then, the user proceeds to stir the specimen mixing it with the reagents and causing a sufficient amount of the liquid part of the mixture to go through the lateral wall of trocar 20''. After sufficiently stirring the specimens and the reagents, a user inserts trocar 20'' in absorbing jacket 70 that includes three layers. The innermost layer 72 is basically made out of an absorbent permeable material that filters the liquid part of the mixture that passed through the lateral wall of trocar 20''. The second layer 74, which is the middle one in the preferred embodiment, is brought in contact with reagents (i.e. hydrogen peroxide) that will detect the occult blood, if it is contained in the specimen in sufficiently large quantities. The third, and outermost, removable layer 76 is made out of an impermeable material that prevents any liquid or moisture from coming out and it is preferably made out of a transparent material so that the detecting reactions of layer 74, which is typically of a characteristic color, can be seen. In this manner, a diagnostic can be readily arrived at with minimum handling of the specimens. In FIG. 11, stirrer member 80' is coaxially mounted within jacket member 30' that is cooperatively received within jacket member 40'.

The foregoing description conveys the best understanding of the objectives and advantages of the present invention. Different embodiments may be made of the inventive concept of this invention. It is to be understood that all matter disclosed herein is to be interpreted merely as illustrative, and not in a limiting sense.

What is claimed is:

1. A kit for collecting specimens, comprising:
   A. an elongated, tubular trocar means for collecting a specimen having first and second open ends and including a permeable lateral wall so that only moisture of the specimen collected can pass through;
   B. first elongated jacket means for cooperatively receiving said first end;
   C. second elongated jacket means for cooperatively receiving said second end and adapted to enclose said elongated trocar means in cooperative combination with said first elongated jacket means;
   D. rubber band means for urging said first and second elongated jacket means against each other; and
   E. mixer means that is cooperatively received within said elongated trocar means and, upon actuation by user, capable of stirring the specimen collected; and
   F. blade means removably mounted on said first end for cutting a section of said specimen having a hollow central opening of substantially the same dimension of said first end.
2. The kit set forth in claim 1 further including:
   G. dividing means for separating the specimens cut by said blade means and collected inside said tubular member.

* * * * *